United States Patent [19]

Szilágyi et al.

[11] Patent Number: 4,829,076
[45] Date of Patent: May 9, 1989

[54] NOVEL DIHYDROPYRIDINES HAVING CALCIUM ANTAGONISTIC AND ANTIHYPERTENSIVE ACTIVITY

[75] Inventors: Géza Szilágyi; Éva Bozó; László Czollner; László Jaszlits; György Rabloczky; József Borsi; István Elekes; Gyöngyi Nagy née Csókás; András Varró; ZSuzanne Láng née Rihmer; György Cseh; Gyula Horváth, all of Budapest; Ilona Bódi, Eger, all of Hungary

[73] Assignee: Alkaloida Vegyeszeti Gyar, Tiszavasvari, Hungary

[21] Appl. No.: 97,111

[22] Filed: Sep. 16, 1987

[30] Foreign Application Priority Data

Sep. 16, 1986 [HU] Hungary ............... 3948/86

[51] Int. Cl.$^4$ ............... C07D 211/86; A61K 31/455
[52] U.S. Cl. ............... 514/356; 514/332; 514/336; 514/344; 546/283; 546/263; 546/286; 546/321
[58] Field of Search ............... 546/283, 263, 286, 321; 514/332, 336, 344, 356

[56] References Cited

U.S. PATENT DOCUMENTS 4,510,310  4/1985  Wehinger et al. ............ 546/321

FOREIGN PATENT DOCUMENTS 3526929  5/1987  Fed. Rep. of Germany .

56956  4/1985  Japan .

Primary Examiner—Jane T. Fan
Attorney, Agent, or Firm—Keil & Weinkauf

[57] ABSTRACT

The invention relates to new substituted dihydropyridine derivatives of the general formula (I),

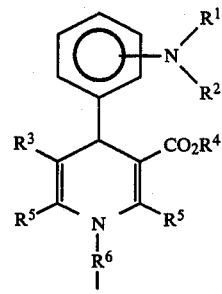

wherein $R^1$ and $R^6$ are as defined herein after, the racemic and optically active variants as well as mixtures thereof, furthermore the acid addition salts of these compounds, pharmaceutical compositions containing the same and a process for the preparation thereof.

The compounds of the general formula (I) can be advantageously applied for the treatment of pathologically severe hypertensions, their toxicity is low and they possess an advantageous therapeutic index.

10 Claims, No Drawings

NOVEL DIHYDROPYRIDINES HAVING CALCIUM ANTAGONISTIC AND ANTIHYPERTENSIVE ACTIVITY

The invention relates to new substituted dihydropyridine derivatives of the general formula (I),

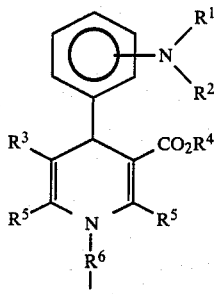

wherein
$R^1$ stands for a hydrogen atom,
$R^2$ stands for a $C_{2-10}$ alkanoyl or $C_{4-7}$ cycloalkancyl group,
or a group of general formula $-CO(CH_2)_m-Ar$, wherein
m is zero to 3 and the $-(CH_2)_m$ alkyl chain is straight-chained or branched, saturated or unsaturated and
Ar represents an unsubstituted aryl group or an aryl group substituted aryl group or an aryl group substituted by a halogen atom, $C_{1-4}$ alkyl group, one or more $C_{1-4}$ alkoxy group(s), $C_{1-4}$ alkylthio, $C_{1-4}$ alkylsulfinyl or $C_{1-4}$ alkylsulfonyl group, trifluoromethyl, nitro, amino or optionally substituted amino group or an aromatic group which may contain a nitrogen and/or oxygen atom,
a trifluoracetyl group or
a group of the general formula $-CO_2R^7$, wherein
$R^7$ stands for a $C_{1-4}$ alkyl group, or
a group of the general formula $-SO_2R^8$, wherein
$R^8$ represents a $C_{1-4}$ alkyl group, unsubstituted phenyl group or a phenyl group substituted by a $C_{1-4}$ alkyl or nitro group,
$R^3$ stands for a cyano or a straight chained or branched alkoxycarbonyl group,
$R^4$ stands for a $C_{1-4}$ straight-chained or branched alkyl or $C_{5-7}$ cycloalkyl group or a $C_{2-6}$ alkoxyalkyl group,
$R^5$ stands for a $C_{1-4}$ alkyl group, and
$R^6$ stands for a hydrogen atom,
the racemic and optically active variants as well as mixtures thereof, furthermore the acid addition salts of these compounds, pharmaceutical compositions containing the same, and a process for the preparation thereof.

It is known that some substituted 1,4-di-hydropyridine derivatives possess favourable pharmacological properties. Such are described in European Patents Nos. 88,903, 94,159 and 106,276. Now it has been found that the new compounds of the general formula (I) of the invention which contain, unlike the known compounds, a phenyl ring substituted by an amide group at position 4 of the dihydropyridine skeleton, possess highly valuable pharmacological properties which are superior to those of the known compounds.

In a preferred group of the compounds of general formula (I) $R^1$ and $R^6$ represent a hydrogen atom, $R^2$ a $C_{2-10}$ alkanoyl group such as acetyl or octanoyl group, or a $C_{4-7}$ cycloalkanoyl group, such as cyclopropanecarbonyl group, $R^3$ stands for a $C_{2-4}$ alkoxycarbonyl group, such as methoxycarbonyl or ethoxycarbonyl group, $R^4$ means a $C_{1-4}$ alkyl group, such as a methyl or ethyl group, and $R^5$ represents a methyl group.

In an other preferred group of the compounds of the general formula (I) $R^1$ and $R^6$ represent a hydrogen atom, $R^2$ stands for a group of general formula $-CO(CH_2)_m-Ar$, wherein m is zero and Ar is unsubstituted pheny or substituted by a halogen atom, nitro, $C_{1-4}$ alkyl, preferably methyl or ethyl group, one or more $C_{1-4}$ alkoxy, preferably methoxy group, methylthio, methylsulfinyl, methylsulfonyl, trifluoromethyl or amino group, or furoyl, nicotinoyl or isonicotinoyl group, $R^3$ stands for a cyano or $C_{2-4}$ alkoxycarbonyl, preferably methoxycarbonyl, ethoxycarbonyl, n-propoxycarbonyl, isopropoxycarbonyl or t-butoxycarbonyl group, $R^4$ means a methyl, ethyl, cyclohexyl or 2-methoxyethyl group and $R^5$ stands for a methyl group.

In a particularly preferred group of the compounds of the general formula (I) $R^1$ and $R^6$ represent a hydrogen atom, $R^2$ stands for a trifluoroacetyl group, $R^3$ means a cyano or $C_{2-4}$ alkoxycarbonyl, preferably methoxycarbonyl group, $R^4$ represents a methyl, ethyl, cyclohexyl or 2-methoxyethyl group and $R^5$ stands for a methyl group.

According to an other aspect of the invention there is provided a process for the preparation of the compounds of general formula (I), which comprises reacting a compound of the general formula (II),

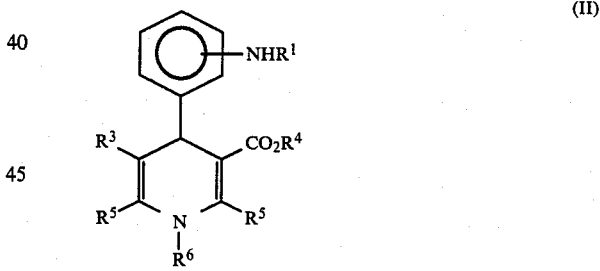

wherein $R^1$, $R^3$, $R^4$, $R^5$ and $R^6$ have the same meaning as above, with a compound of the general formula (III),

$$R^2-X \qquad (III)$$

wherein $R^2$ has the same meaning as above, and X is a leaving group suitable for the introduction of $R^2$, and if desired, a compound of the general formula (I)—wherein $R^1$, $R^3$, $R^4$, $R^5$ and $R^6$ have the same meaning as above but $R^2$ represents a group of the general formula $-CO(CH_2)_mAr$, wherein m is zero and Ar stands for an aryl group substituted by a nitro group—is reduced by a known method, and then, if desired, the free base of the general formula (I) obtained by the above methods is converted to an acid addition salt.

According to the definition accepted in the literature (see T. A. Geissmann: Principles of Organic Chemistry, ed. 3, Editor W. H. Freeman, London, 1968) "leaving group" X is considered a group which can be easily displaced by a nucleophilic agent. Such groups are the halogen atoms, particularly chlorine, bromine and iodine atoms, furthermore acetoxy or trifluoroacetoxy groups. On carrying out the process of the invention chlorine is a particularly preferred X group.

In a preferred embodiment of the process of the invention 1.1 to 2.5 moles of a compound of the general formula (III) is added to a solution of 1 mole of a compound of the general formula (II) in an organic solvent, preferably dioxane or benzene, at zero to 30° C., preferably at 5° to 15° C., if desired, in the presence of 1.1 to 2.0 moles of an organic base, e.g. pyridine, and the reaction mixture is stirred for 1 to 20 hours at room temperature. After completed reaction the reaction mixture is poured into water, the pH of the mixture is neutralized with an acid, the precipitate formed is filtered and, if desired, purified by recrystallization. $C_{1-4}$ alcohols, such as ethanol, are preferably used as recrystallizing solvents.

Acid chlorides, acyl anhydrides, dialkylpyrocarbonates or chloroformic esters are preferably used as compounds of the general formula (III).

Those compounds of the general formula (I) wherein the aryl group in $R^2$ is substituted by a nitro group, e.g. nitrophenyl group, can be reduced to an amino group by known methods. Reduction can be preferably performed by catalytic hydrogenolysis in a $C_{1-4}$ alkanol, at room temperature and atmospheric pressure, applying Pd-C as catalyst.

The compounds of general formula (I) comprising a basic nitrogen as substituent, and prepared by the process of the invention, can be converted in a protic solvent, such as isopropanol, with an inorganic or organic acid, such as hydrochloric acid, maleic acid, or fumaric acid to a suitable acid addition salt. This salt can be prepared by a known method, e.g. by dissolving the base in an organic alcoholic solvent and adding the required acid or a solution thereof in alcoholic organic solvent. The salt obtained is separated either by filtering or by evaporating the solvent and, if desired, it is purified by recrystallisation.

The starting materials of the general formula (II), used in the process of the invention, are partly described in the literature [J. Am. Chem. Soc., 71, 4003 (1949), South African Patent Specification No. 68 01482] or are prepared analogously.

The compounds of the general formula (III) are commercially available compounds.

The compounds of the general formula (I) of the invention possess valuable therapeutic, particularly calcium-antagonistic and antihypertensive properties. Their favourable therapeutic action is manifested in a direct vasodilating activity in the coronary, cerebral and peripheral system. Consequently, their application is recommended primarily in cerebral, cardiac and peripheral vascular diseases, such as myocardial ischemia, cerebral hemorrhage, cerebral infarction, temporary cerebral vascular dysfunction, atherosclerosis, renal arteriostenosis and various further stenotic conditions.

It is a further advantageous property of these compounds that unlike beta-receptor blockers, they have no bronchoconstrictive activity and can thus be applied also in asthmatic patients.

Furthermore, their vascular and cardioprotective potency is of major importance as this can be favourably used in the therapy of vascular diseases and angina pectoris.

They are also superior compared to agents of similar indication as they fail to exert negative inotropic side effects.

Furthermore, the compounds of general formula (I) also possess uterus relaxant activity, they inhibit the uterus contracting effect of $PGF_{2alpha}$ in the isolated rat uterus at low concentrations.

In vitro uterus relaxant activity in the isolated rat uterus

The test was performed according to the method of Gaddum and Hammeed [Brit. J. Pharmacol. 9:240 (1954)]. The inhibitory activity of $10^{-6}$ M doses of the test compounds on the $PGF_{2alpha}$ induced uterus contractions was determined. Nifedipine [2,6-dimethyl-4-(2-nitrophenyl)-1,4-dihydro-pyridine-3,5-dicarboxylic acid methyl ester] served as reference compound. The results are presented in Table 1 showing that the compounds of the invention are equiactive to the reference compound.

TABLE 1

| $PGF_{2alpha}$ inhibitory effect of the compounds of general formula (I) | | |
|---|---|---|
| Compound Example No | Concentration of test compound M | Inhibition of $PGF_{2alpha}$ induced contraction % |
| 8 | $10^{-6}$ | 96.7 |
| 9 | $10^{-6}$ | 94.3 |
| 10 | $10^{-6}$ | 94.0 |
| 11 | $10^{-6}$ | 77.8 |
| 12 | $10^{-6}$ | 83.3 |
| 34 | $10^{-6}$ | 98.0 |
| 42 | $10^{-6}$ | 88.0 |
| Nifedipine | $10^{-6}$ | 95.0 |

The antihypertensive effect of the compounds of the general formula (I) of the invention was determined by in vivo experiments according to the following methods.

Hypotensive effect in anesthetized cats

A tube was inserted in the trachea of cats anesthetized with ip.35 mg/kg of pentobarbital sodium to ensure spontaneous respiration. The femoral artery and vein were both cannulated unilaterally. The vegetative test compounds (adrenaline, isoproterenol) were administered through the venous cannule. The mean arterial blood pressure was measured by joining the arterial cannule to a Statham P23Db pressure transducer and electromanometer. The heart rate was determined by a cardiotachometer triggered by arterial pulse-wave.

Various doses of the test compounds were administered through a cannule inserted into the duodenum. The results are presented in Table 2.

Antihypertensive effect in spontaneously hypertensive conscious rats ("SH" rats)

The systolic blood pressure was indirectly measured by the tail-cuff method in "SH" rats (Wistar-Okamoto) [Arzneimittel-Forschung 6, 222 (1956)]. The blood pressure of rats was measured before treatment and hourly after drug administration till the 24th posttreatment hour. The test compounds were administered orally, by gavage. Table 3 presents the effect of some compounds of the invention.

Antihypertensive effect in rats with renal hypertension ("RH" rats)

The test was performed according to the method of Grollman [Proc. Soc. Exptl. Biol. Med. 57, 102 (1944)] in CFY male rats weighing 120 to 150 g. Five to six weeks after surgery the systolic blood pressure of the rats attained 180 to 220 Hgmm. The test compounds were administered orally. The results are presented in Table 4.

Antihypertensive effect in rats with DOCA-induced hypertension ("DH" rats)

The test was performed according to Cunning et al. [J. Pharm. Exp. Ther. 161, 88 (1981)]. The results are presented in Table 5.

The data of Tables 2 to 5 demonstrate that the compounds of general formula (I) exert significant antihypertensive effect at both intraduodenal and oral administration, some attaining the activity of the reference compound Nifedipine and some being even superior.

TABLE 2

Hypotensive effect of compounds of general formula /I/ in anesthetized, normotensive cats Dose: 1 mg/kg id.

| Example No. | MEAN ARTERIAL PRESSURE (Hgmm) | | | | | |
|---|---|---|---|---|---|---|
| | 0 min | 5 min | 15 min | 30 min | 60 min | 120 min |
| 6 | 120 | 115 | 85 | 65 | 70 | 75 |
| 7 | 145 | 115 | 60 | 50 | 60 | 85 |
| 9 | 135 | 125 | 85 | 65 | 75 | 102 |
| 10 | 140 | 60 | 70 | 80 | 85 | — |
| 11 | 152 | 147 | 130 | 125 | 120 | 132 |
| 12 | 145 | 115 | 92 | 90 | 97 | 145 |
| 14 | 165 | 150 | 75 | 85 | 95 | 110 |
| 15 | 103 | 90 | 65 | 65 | 73 | 90 |
| 18 | 120 | 75 | 00 | 100 | 100 | — |
| 20 | 160 | 140 | 00 | 105 | 105 | 120 |
| 21 | 140 | 90 | 95 | 100 | 110 | 110 |
| 22 | 125 | 120 | 110 | 105 | 85 | 85 |
| 28 | 142 | 137 | 105 | 97 | 100 | 115 |
| 34 | 135 | 90 | 60 | 75 | 90 | 105 |
| 37 | 155 | 150 | 100 | 100 | 100 | 135 |
| 41 | 100 | 90 | 80 | 85 | 10 | — |

TABLE 3

Antihypertensive effect of compounds of general formula /I/ in spontaneously hypertensive conscious rats

| Example No. | Dose (mg/kg) p.o. | Systolic blood pressure in Hgmm and reduction in % | | | | | | | |
|---|---|---|---|---|---|---|---|---|---|
| | | $0^h$ | % | $2^h$ | % | $5^h$ | % | $24^h$ | % |
| 7 | 5 | 206 | 100 | 175.2 | −15 | 157.6 | −24 | 217.6 | +5 |
| | 10 | 226 | 100 | 164.0 | −28 | 164.0 | −28 | 230.0 | +1 |
| 9 | 10 | 190 | 100 | 166.6 | −13 | 166.6 | −13 | 192.0 | +1 |
| 11 | 10 | 187.6 | 100 | 140 | −26 | 157.8 | −16 | 178.8 | −5 |
| 12 | 10 | 190 | 100 | 164 | −14 | 166.0 | −13 | 190.8 | 0 |
| 14 | 10 | 198 | 100 | 165 | −17 | 164.5 | −17 | 206.8 | +4 |
| 15 | 2.5 | 203.8 | 100 | 141.4 | −31 | 139.2 | −32 | 193.8 | −5 |
| 18 | 10 | 200 | 100 | 179.2 | −11 | 178 | −11 | 192.6 | −4 |
| 21 | 10 | 193.6 | 100 | 175.2 | −10 | 167.8 | −14 | 201.4 | +4 |
| 22 | 2.5 | 193.9 | 100 | 142.2 | −27 | 144.0 | −26 | 191.4 | −2 |
| 28 | 10 | 194 | 100 | 174.8 | −10 | 163.5 | −16 | 202.4 | +4 |
| 34 | 10 | 224 | 100 | 170.0 | −25 | 182.0 | −19 | 216.0 | −4 |
| 36 | 10 | 212 | 100 | 172.8 | −19 | 172.4 | −19 | 222.0 | +4 |
| Nifedipine | 5 | 219.7 | 100 | 167.3 | −24 | 181.0 | −18 | 210.0 | −8 |
| | 10 | 218.2 | 100 | 139.2 | −37 | 147.1 | −33 | 198.5 | −10 |

TABLE 4

Antihypertensive effect of compounds of Examples 7 and 34 in conscious rats with renal hypertension

| Example No. | Dose (mg/kg) p.o. | Systolic blood pressure in Hgmm and pressure reduction in % | | | | | | | |
|---|---|---|---|---|---|---|---|---|---|
| | | $0^h$ | % | $2^h$ | % | $5^h$ | % | $24^h$ | % |
| 7 | 5 | 206.6 | 100 | 177.7 | −15 | 188.6 | −13 | 213.3 | +3 |
| | 10 | 198.8 | 100 | 138.8 | −31 | 150.0 | −25 | 212.2 | +6 |
| 34 | 10 | 198.0 | 100 | 141.0 | −28 | 167.0 | −14 | 199.0 | 0 |
| Nifedipine | 5 | 173.5 | 100 | 141.0 | −19 | 147.5 | −15 | 173.5 | 0 |
| | 10 | 195.7 | 100 | 163.3 | −31 | 131.1 | −34 | 194.6 | −1 |

TABLE 5

Antihypertensive effect of compounds of Examples 7 and 34 in conscious rats with DOCA-induced hypertension

| Example No. | Dose (mg/kg) p.o. | Systolic blood pressure in Hgmm and pressure reduction in % | | | | | | | |
|---|---|---|---|---|---|---|---|---|---|
| | | $0^h$ | % | $2^h$ | % | $5^h$ | % | $24^h$ | % |
| 7 | 5 | 176.8 | 100 | 135.7 | −24 | 149.4 | −16 | 180.8 | +2 |
| | 10 | 176.2 | 100 | 126.7 | −28 | 147.5 | −17 | 177.5 | 0 |
| 34 | 5 | 192.0 | 100 | 150.0 | −22 | 163.0 | −16 | 193.0 | 0 |
| | 10 | 189.0 | 100 | 146.0 | −23 | 134.0 | −30 | 186.0 | −2 |

The calcium-antagonistic effect of the compounds of general formula (I) of the invention was tested by in vitro experiments according to the following methods.

Calcium-antagonistic effect on an isolated vessel preparation

The experiments were performed according to the method of M. Fiol de Cuneo et al. [Arch. Int. Pharmacodyn. Ther. 263, 28 (1983)]. Portal veins were obtained from decapitated male rats weighing 300 to 350 g. The longitudinally incised venous segment was suspended in an organ chamber (10 ml) filled with physiological saline solution under resting tension of 1 g. Its upper end was attached to a HSI force-displacement transducer. Isometric contractions were recorded with a Beckman Dynograph.

After the initial equilibration period in a calcium-free Krebs-Ringer bicarbonate solution (KRB) the vein was exposed to a depolarizing solution (calcium-free KRB containing 90 mM of KCl) for 10 minutes. In order to determine the cumulative contractile responses $CaCl_2$ was added in an end-concentration of 2.5 and 5.0 mM, resp. Each medium was oxygenated with carbogen gas and maintained at 37° C. and pH 7.4.

The influence of the test compounds on the contraction was determined by incubating the veins in the depolarizing solution for 10 minutes before and during exposure to $Ca^{2+}$. Each vein preparation was subjected to a single concentration of the test compound.

For each experiment the 100% responses were considered as the maximum contractile responses during the control Ca curves. The contractions after exposure to the test compounds were expressed as the percentage of these values. The concentration producing a 50% inhibition of the maximum response relative to the control curve ($IC_{50}$, M) was estimated from the concentration-response curves by plotting the percentual inhibition of the contractile response against the concentration of the test compound. Throughout the experiments Nifedipine served as the reference compound.

Receptor binding studies

Among the structurally diverse groups of calcium antagonists there are some drugs which specifically block the function of calcium channels by interacting with highly specific receptor site(s) of the sarcolemmal membrane. In the 1,4-dihydro-pyridine series the ligand property of a compound can be analyzed by studying its effect on the specific binding of $^3H$-nitrendipine, a potent analogue of Nifedipine, to the heart microsomal preparation [G. T. Bolger, P. J. Gengo, E. M. Luchowski, H. Siegel, D. J. Triggle and R. A. Janis: Biochem. Biophys. Res. Comm. 104, 1604 (1982)]. The competition of the compounds of the invention for the 1,4-dihydropyridine receptor sites was studied with this technique and the activities were expressed by the concentration ($IC_{50}$) displacing 50% of the $^3H$-nitrendipine bound to the receptor preparation under the test conditions applied. The results obtained are presented in Table 7.

The sub-low micromolar range of $IC_{50}$ values indicates that the compounds of the invention exert high affinity to the 7-dihydropyridine receptor site. It is, however, worth to mention that the activity of the new compounds was found to be slightly less than that of references. This finding suggests that a more active coupling mechanism between receptor stimulation and biological response may exist in the case of the new compounds of the invention.

TABLE 6

Calcium-antagonistic effect of the compounds of general formula (I)

| Compound of Example | Inhibition of the potential-mediated calcium channel, $IC_{50}$, M |
| --- | --- |
| 7 | $5 \times 10^{-10}$ |
| 15 | $3 \times 10^{-9}$ |
| 34 | $2.5 \times 10^{-9}$ |
| Nifedipine /reference/ | $2 \times 10^{-9}$ |

TABLE 7

Receptor binding of the compounds of general formula (I)

| Compound of Example | $IC_{50} /10^{-9}$ M/ |
| --- | --- |
| 7 | $6.3 \pm 0.05$ |
| 15 | $15.5 \pm 3.5$ |
| 34 | $16.0 \pm 1.6$ |
| Nitrendipine | $1.25 \pm 0.15$ |
| Nifedipine /reference/ | $4.3 \pm 0.04$ |

On the basis of the pharmacological results, the compounds of general formula (I) of the invention can be advantageously applied for the treatment of pathologically severe hypertensions. It is a major advantage that they do not increase the heart rate, sporadically even bradycardia was found, they have no CNS effects and their good enteral absorption might ensure favourable bioavailability. Their toxicity is generally low, consequently they possess an advantageous therapeutic index.

For therapeutic purposes the daily dose of the compounds of the invention amounts generally to 0.05 mg/kg body weight to 2.0 mg/kg body weight, preferably to 0.1 mg/kg body weight to 0.5 mg/kg body weight, which may be administered in several portions according to the requirements of absorption.

For therapeutical use the active compounds of the invention are suitably formulated to pharmaceutical compositions by mixing them with the commonly used, nontoxic, inert, solid or liquid pharmaceutical carriers and/or additives useful for enteral or parenteral administration. As carriers water, gelatine, lactose, starch, pectin, magnesium stearate, stearic acid, talc or vegetable oils can be used. As additives preservatives and wetting as well as emulsifying, dispersing and aromatizing agents and buffers can be employed.

By using the above-mentioned carriers and additives, the active agents of the invention may be transformed to the usual pharmaceutical compositions, e.g. to solid compositions (such as tablets, capsules, pills or suppositories) or liquid compositions (such as aqueous or oily solutions, suspensions, emulsions or syrups) as well as to injectable solutions, suspensions or emulsions. The invention is illustrated in detail by the following non-limiting Examples.

EXAMPLE 1

4-(2-Acetamidophenyl)-2,6-dimethyl-3,5-bis(methoxycarbonyl)-1,4-dihydropyridine

To a solution of 315 mg(1 mmole) of 4-(2-aminophenyl)-2,6-dimethyl-3,5-bis(methoxycarbonyl)-1,4-dihydropyridine [J. Am. Chem. Soc., 71, 4003 (1949)] in 1 ml of dioxane and 1 ml of pyridine a solution of 0.18 g of acetylchloride in 1 ml of dioxane was added dropwise during 20 minutes in a temperature range of 0° to 10° C., then the mixture was stirred for 40 minutes at this temperature and for 3 hours at room temperature, thereafter it was poured into 10 ml of aqueous 10% hydrochloric acid. The precipitate formed was filtered, washed with water and dried. Yield 350 g (97.5%), m.p. 284° to 285° C. (ethanol).

The method used in Example 1 was applied for preparing the following compounds summed up in Table 8.

EXAMPLE 36

2,6-Dimethyl-3-methoxycarbonyl-5-(2-methoxyethoxycarbonyl)-4-(2-trifluoroacetamidophenyl)-1,4-dihydropyridine Yield 19%, m.p. 74°–5° C.

TABLE 8

Compounds of general formula /I/ wherein $R^1$ and $R^6$ represent a hydrogen atom and $R^5$ means a methyl group

| Example No. | $R^2$ | $R^3$ | $R^4$ | Position of acylamide | Yield % | M.p. °C. |
|---|---|---|---|---|---|---|
| 2 | Acetyl | Methoxycarbonyl | Methyl | 3 | 86.5 | 232–3 |
| 3 | 4-Chlorobenzoyl | Methoxycarbonyl | Methyl | 3 | 76 | 250–2 |
| 4 | 4-Nitrobenzoyl | Methoxycarbonyl | Methyl | 3 | 57 | 272–4 |
| 5 | 4-Methylbenzoyl | Methoxycarbonyl | Methyl | 3 | 69 | 210–1 |
| 6 | 4-Chlorobenzoyl | Methoxycarbonyl | Methyl | 2 | 45 | 278–80 |
| 7 | 4-Nitrobenzoyl | Methoxycarbonyl | Methyl | 2 | 70 | 261–2 |
| 8 | 2-Nitrobenzoyl | Methoxycarbonyl | Methyl | 2 | 52 | 268–70 |
| 9 | Cinnamoyl | Methoxycarbonyl | Methyl | 2 | 41 | 144–6 |
| 10 | Furoyl | Methoxycarbonyl | Methyl | 2 | 32 | 283–5 |
| 11 | 4-Nitrocinnamoyl | Methoxycarbonyl | Methyl | 2 | 38 | 248–50 |
| 12 | Benzoyl | Methoxycarbonyl | Methyl | 2 | 38 | 257–9 |
| 13 | 3-Nitrobenzoyl | Methoxycarbonyl | Methyl | 2 | 40 | 281–3 |
| 14 | 4-Methoxybenzoyl | Methoxycarbonyl | Methyl | 2 | 32 | 235–6 |
| 15 | 4-Methylbenzoyl | Methoxycarbonyl | Methyl | 2 | 81 | 222–3 |
| 16 | 3,4-Dimethoxybenzoyl | Methoxycarbonyl | Methyl | 2 | 25 | 252–3 |
| 17 | 3,4,5-Trimethoxybenzoyl | Methoxycarbonyl | Methyl | 2 | 31 | 247–8 |
| 18 | Octanoyl | Methoxycarbonyl | Methyl | 2 | 45 | 99–100 |
| 19 | Cyclopropanecarbonyl | Methoxycarbonyl | Methyl | 2 | 67 | 224–6 |
| 20 | 3-Methylbenzoyl | Methoxycarbonyl | Methyl | 2 | 44 | 236–7 |
| 21 | 2-Methylbenzoyl | Methoxycarbonyl | Methyl | 2 | 59 | 231–2 |
| 22 | 4-Ethylbenzoyl | Methoxycarbonyl | Methyl | 2 | 31 | 222–3 |
| 23 | Phenylacetyl | Methoxycarbonyl | Methyl | 2 | 52 | 240–1 |
| 24 | Nicotinoyl | Methoxycarbonyl | Methyl | 2 | 75 | 230–40 |
| 25 | Isonicotinoyl | Methoxycarbonyl | Methyl | 2 | 45 | 241–2 |
| 26 | 3-Trifluoromethylbenzoyl | Methoxycarbonyl | Methyl | 2 | 33 | 215–6 |
| 27 | 4-Methylsulfonylbenzoyl | Methoxycarbonyl | Methyl | 2 | 32 | 228–30 |
| 28 | 4-Nitrobenzoyl | Methoxycarbonyl | 2-Methoxyethyl | 2 | 33 | 128–30 |
| 29 | 4-Nitrobonzoyl | Methoxycarbonyl | Cyclohexyl | 2 | 36 | 208–10 |
| 30 | 2-Methylthiobenzoyl | Methoxycarbonyl | Methyl | 2 | 80 | 255–6 |
| 31 | 2-Methylsulfinylbenzoyl | Methoxycarbonyl | Methyl | 2 | | |
| 32 | 4-Methylbenzoyl | t-Butoxycarbonyl | Methyl | 2 | 37 | 261–3 |

EXAMPLE 33

2,6-Dimethyl-3,5-bis(methoxycarbonyl)-4-(3-trifluoroacetamidophenyl)-1,4-dihydropyridine A mixture of 630 mg (2 mmoles) of 4-(3-aminophenyl)-2,6-dimethyl-3,5-bis(methoxycarbonyl)-1,4-dihydropyridine, 420 mg (4 mmoles) of trifluoroacetic anhydride and 0.18 g (23 mmoles) of pyridine is stirred between 5° and 10° C., then 2.3 ml of pyridine are added drop-wise during 25 minutes. Stirring is continued at room temperature for 24 hours. The reaction mixture is thereafter processed as described in Example 1. Yield 285 mg (35%), m. p. 231°–2° C. (ethanol).

Applying the procedure described in Example 33 the following compounds are prepared:

EXAMPLE 34

2,6-Dimethyl-3,5-bis(methoxycarbonyl)-4-(2-trifluoroacetamidophenyl)-1,4-dihydropyridine Yield 76%, m. p. 239°–40° C.

EXAMPLE 35

2,6-Dimethyl-3,5-bis(ethoxycarbonyl)-4-(2-trifluoroacetamidophenyl)-1,4-dihydropyridine Yield 37%, m. p. 214°–° C.

EXAMPLE 37

2,6-Dimethyl-3-isopropoxycarbonyl-5-methoxycarbonyl-4-(2-trifluoroacetamidophenyl)-1,4-dihydrophyridine Yield 50%, m.p. 207°–° C.

EXAMPLE 38

2,6-Dimethyl-4-(3-ethoxycarbonylaminophenyl)-3,5-bis(methoxycarbonyl)11,4-dihydropyridine A mixture of 500 mg of 4-(3-aminophenyl)-2,6-dimethyl-3,5-bis(methoxycarbonyl)-1,4dihydropyridine, 5 ml of dichloromethane and 500 mg of diethylpyrocarbonate are stirred at room temperature for 3 hours, then left to stand overnight and thereafter evaporated to dryness at reduced pressure.

Yield 450 mg (73%), m.p. 183°–5° C. (ethanol)

Applying the procedure described in Example 38 the following compound is prepared:

EXAMPLE 39

2,6-Dimethyl-4-(2-ethoxycarbonylaminophenyl)-3,5-bis(methoxycarbonyl)-1,4-dihydropyridine Yield 32%, m.p. 182°–3° C.

EXAMPLE 40

2,6-Dimethyl-4-(3-methanesulfonylamidophenyl)-3,5-bis(methoxycarbonyl)-1,4-dihydropyridine To a stirred mixture of 1.14 g n3.6 mmoles) of 4-(3-aminophenyl)-2,6-dimethyl-3,5-bis(methoxycarbonyl)-1,4-dihydropyridine and 4 ml of pyridine 0.7 g (6.14 mmoles) of methansulfonylchloride are added drop-wise during 30 minutes at 5° C. Stirring is continued for 24 hours at room temperature, then the reaction mixture is poured into an aqueous 4% hydrochloric acid solution, the precipitate formed is filtered, washed with water and refluxed with ethanol.

Yield 1.2 g (86%), m.p. 225°–6° C. Applying the procedure described in Example 40 the following compounds are prepared:

EXAMPLE 41

2,6-Dimethyl-4-n2-methanesulfonylamidophenyl)-3,5-bis(methoxycarbonyle-1,4-dihydropyridine Yield 43%, m.p. 224°–° C.

EXAMPLE 42

2,6-Dimethyl-3,5bis(methoxycarbonyl)-4-[2-(4-nitrobenzenesulfonamido)-phenyl]-1,4-dihydropyridine Yield 35%, m.p. 203°–° C.

EXAMPLE 43

2,6-Dimethyl-4[2-(4-methylbenzenesulfonamido)-phenyl]-3,5bis(methoxycarbonyl)-1,4-dihydropyridine Yield 66%, m.p. 167°–9° C.

EXAMPLE 44

2,6-Dimethyl-4-[2-(4-benzenesulfonamido)-phenyl]-3,5-bis(methoxycarbonyl)-1,4-dihydropyridine Yield 12%, m.p. 209°–211° C.

EXAMPLE 45

2,6-Dimethyl-3-methoxycarbonyl-5-cyano-4-[2-(4-nitrobenzamido)-phenyl]-1,4-dihydropyridine To a solution of 0.85 g (3 mmoles) of 5-cyano-2,6dimethyl-3-methoxycarbonyl-4-(2-aminophenyl)-1,4-dihydropyridine in 8.5 ml of anhydrous dioxane 0.4 ml (5 mmoles) of pyridine are added. The solution is cooled to 15° C., then a solution of 0.6 g (3.3 mmoles) of 4-nitrobenzoylchloride in 4 ml of anhydrous dioxane is added drop-wise. The reaction mixture is stirred at room temperature for 15 hours, then it is poured into water. The precipitated crystals are filtered and recrystallized from a mixture of dimethylsulfoxide and ethanol.

Yield 0.85 g (66%), m.p. 274°–7° C.

5-Cyano-2,6dimethyl-3-methoxycarbonyl-4-(2-aminophenyl)-1,4-dihydropyridine used as starting material is prepared by the following method: The solution of 0.8 g (2.5 mmoles) of 5cyano-2,6-dimethyl-3-methoxycarbonyl-4-(2-nitrophenyl)-1,4- (2-nitrophenyl-1,4-dihydropyridine (published German patent application No. 2,658,804) in 80 ml of methanol is submitted to hydrogenolysis in the presence of Pd-C at atmospheric pressure. After completed reduction the catalyst is filtered and washed with hot methanol. The solvent is evaporated and the residue is recrystallized from ethanol.

Yield 0.6 g (83%), m.p. 207°–210° C.

Applying the procedure described in Example 45 the following compounds listed in Table 9 are prepared:

TABLE 9

Compounds of general formula /I/ wherein $R^1$ and $R^6$ represent a hydrogen atom and $R^5$ means a methyl group

| Example No. | $R^2$ | $R^3$ | $R^4$ | Position of acyl-amide | Yield % | M.p. °C. |
|---|---|---|---|---|---|---|
| 46 | 4-Chlorobenzoyl | Cyano | Methyl | 3 | 88 | 252–4 |
| 47 | 4-Nitrobenzoyl | Cyano | Methyl | 3 | 65 | 278–280 |
| 48 | 4-Nitrobenzoyl | Cyano | Ethyl | 3 | 67 | 271–3 |
| 49 | 4-Methoxybenzoyl | Cyano | Methyl | 2 | 37 | 129–131 |
| 50 | 4-Methoxybenzoyl | Cyano | Methyl | 3 | 40 | 226–8 |
| 51 | 4-Methylbenzoyl | Cyano | Methyl | 2 | 71 | 244–6 |
| 52 | 4-Methylbenzoyl | Cyano | Methyl | 3 | 78 | 233–5 |
| Compounds prepared according to Example 33: | | | | | | |
| 53 | Trifluoroacetyl | Cyano | Methyl | 3 | 75 | 229–231 |
| 54 | Trifluoroacetyl | Cyano | Ethyl | 3 | 76 | 226–8 |

EXAMPLE 55

4-[2-(4-Aminobenzamido)-phenyl]-2,6dimethyl-3,5-bis(-methoxycarbonyl)-1,4-dihydropyridine The solution of 2.8 g (60 mmoles) of 4-[2-(4-nitrobenzamido)-phenyl]-2,6-dimethyl-3,5-bis(methoxycarbonyl)-1,4dithydropyridine, prepared according to Example 4, is submitted to hydrogenolysis for 2 hours in 100 ml of anhydrous methanol, in the presence of 1.8 g of 10% Pd-C. After completed reaction the catalyst is filtered, washed three times with 25 ml of hot acetone, then with 25 ml of acetonitrile. The solvent is evaporated at reduced pressure and the residue is thoroughly washed three times with water, thereafter it is dried.

Yield 2.4 g (91.5%), m.p. 266°–7° C.

Preparation of pharmaceutical compositions

EXAMPLE 56

Preparation of tablets

| Composition (for 1000 tablets) | g |
|---|---|
| 2,6-Dimethyl-3,5-bis(methoxycarbonyl)-4-[2-(tri-fluoroacetamido)-pheny]-1,4-dihydropyridine | 10 |
| Lactose | 185 |
| Microcrystalline cellulose | 25 |
| Talc | 5 |
| Corn starch | 73 |
| Magnesium stearate | 2 |
| total | 300 |

The above ingredients are mixed and homogenized, then the mixture is compressed to tablets containing 10 mg of the active ingredient each.

EXAMPLE 57

Preparation of an injectable solution

| Composition (for 2 liters of solution) | g |
| --- | --- |
| 2,6-Dimethyl- 3,5-bis(methoxycarbonyl)-4-[2-(trifluoroacetamido)-phenyl]-1,4-dihydropyridine | 2 |
| Sodium chloride | 20 |
| Water for injection purposes q.s. ad | 2000 ml |

What we claim is:

1. A dihydropyridine of the formula (I)

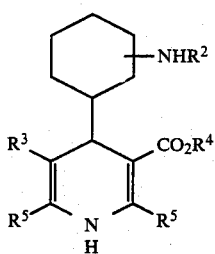

(I)

wherein $R^2$ is a group of the formula —CO—W—Ar, wherein
W is a bond, lower alkylene or alkylydene; and
Ar is an unsubstituted phenyl, a phenyl substituted by a halogen atom, a $C_{1-4}$ alkyl group, one to three $C_{1-4}$ alkoxy, $C_{1-4}$ alkylthio, $C_{1-4}$ alkysulfinyl, $C_{1-4}$ alkylsulfonyl group(s), a trifluoromethyl group, a nitro group or an amino group, a furyl, a nicotinyl, or an isonicotinyl group;
a trifluoroacetyl group;
a group of the formula —$CO_2R^7$, wherein $R^7$ is a $C_{1-4}$ alkyl group; or
a group of the formula —$SO_2R^8$, wherein $R^8$ is a $C_{1-4}$ alkyl, an unsubstituted phenyl or a phenyl substituted by a $C_{1-4}$ alkyl group or a nitro group;
$R^3$ is a cyano or a $C_{2-5}$ straight-chain or branched alkoxycarbonyl group;
$R^4$ is a $C_{1-4}$ straight-chained or branched alkyl, a $C_{5-7}$ cycloalkyl or a $C_{2-6}$ alkoxyalkyl group; and
$R^5$ is a $C_{1-4}$ alkyl group;
the racemate, optically active isomer or an acid addition salt thereof.

2. The dihydropyridine of claim 1 in which $r^2$ is a group of the formula —CO—W—Ar wherein W is a bond and Ar is a unsubstituted phenyl or a phenyl substituted by a halogen atom, a $C_{1-4}$, alkyl group, one to three $C_{1-4}$ alkoxy, $C_{1-4}$ alkylthio, $C_{1-4}$ alkylsulfinyl, $C_{1-4}$ alkylsulfonyl group(s), a trifluoromethyl 3. The dihydropyridine of claim 1 in which $R_2$ is a trifluoroacetyl group.

4. 2,6-dimethyl-3,5bis(methoxycarbonyl)-4-[2(4-nitrobenzamido)-phenyl]-1,4-dihydropyridine.

5. 2,6-dimethyl-3,5-bis(methoxycarbonyl)-4-[2-(4-methylbenzamido)-phenyl]-1,4-dihydropyridine.

6. 2,6-dimethyl-3,5-bis(methoxycarbonyl)-4-[2-(4-ethylbenzamido)-phenyl]-1,4-dihydropyridine.

7. 2,6-dimethyl-3,5-bis(methoxycarbonyl)-4-[2-(4-trifluoroacetamido)-phenyl]-1,4-dihydropyridine.

8. A pharmaceutical composition having calcium antagonistic and antihypertensive effects comprising an effective amount of the dihydropyridine of claim 1 or the racemate, optically active isomer or pharmaceutically acceptable acid addition salt thereof in admixture with pharmaceutically acceptable carriers, additives or mixtures thereof.

9. A method of treating hypertension by administering to an individual in need thereof an effective amount of the composition of claim 8.

10. A method of inhibiting uterine contractions by administering to an individual in need thereof an effective amount of the composition of claim 8.

* * * * *

UNITED STATES PATENT AND TRADEMARK OFFICE
CERTIFICATE OF CORRECTION

PATENT NO. : 4,829,076
DATED : May 9, 1989
INVENTOR(S) : Szilagy et al.

It is certified that error appears in the above-identified patent and that said Letters Patent is hereby corrected as shown below:

IN THE CLAIMS

Claim 2, Line 1

"of claim 1 in which $r^2$ is a group of the formula"

Should read

"of claim 1 in which $R^2$ is a group of the formula"

Claim 2, Line 6

"$C_{1-4}$ alkylsulfonyl group(s), a trifluoromethyl"

Should read

"$C_{1-4}$ alkylsulfonyl group(s), a trifluoromethyl group, a nitro group or an amino group."

Signed and Sealed this

Seventeenth Day of October, 1989

*Attest:*

DONALD J. QUIGG

*Attesting Officer*     *Commissioner of Patents and Trademarks*